United States Patent
Rönnberg et al.

(10) Patent No.: US 10,729,601 B2
(45) Date of Patent: Aug. 4, 2020

(54) ABSORBENT PRODUCTS COMPRISING FOAM MATERIAL

(71) Applicant: ESSITY HYGIENE AND HEALTH AKTIEBOLAG, Göteborg (SE)

(72) Inventors: Peter Rönnberg, Göteborg (SE); Philip Blomström, Göteborg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 0 days.

(21) Appl. No.: 16/466,443

(22) PCT Filed: Dec. 5, 2016

(86) PCT No.: PCT/SE2016/051217
§ 371 (c)(1),
(2) Date: Jun. 4, 2019

(87) PCT Pub. No.: WO2018/106158
PCT Pub. Date: Jun. 14, 2018

(65) Prior Publication Data
US 2020/0069485 A1  Mar. 5, 2020

(51) Int. Cl.
*A61F 13/537* (2006.01)
*A61F 13/47* (2006.01)
(Continued)

(52) U.S. Cl.
CPC .. *A61F 13/53747* (2013.01); *A61F 13/15723* (2013.01); *A61F 13/513* (2013.01);
(Continued)

(58) Field of Classification Search
CPC .... A61F 13/53747; A61F 2013/530861; A61F 13/53713; A61F 2013/530802–530854; A61F 13/47
See application file for complete search history.

(56) References Cited

U.S. PATENT DOCUMENTS 4,389,211 A * 6/1983 Lenaghan ......... A61F 13/15203
604/383
5,397,316 A * 3/1995 LaVon .................. A61F 13/535
604/369
(Continued)

FOREIGN PATENT DOCUMENTS

CN    102006847 A    4/2011
CN    105101926 A    11/2015
(Continued)

OTHER PUBLICATIONS

First Chinese Office Action dated Nov. 22, 2019 issued in Chinese patent application No. 201680091298.9 (7 pages) and its English-language translation thereof (7 pages).
(Continued)

Primary Examiner — Susan S Su
(74) Attorney, Agent, or Firm — Faegre Drinker Biddle & Reath LLP

(57) ABSTRACT

An absorbent product includes a liquid permeable topsheet, a liquid impermeable backsheet, and an absorbent core enclosed between the topsheet and the backsheet. The absorbent core includes an absorbent fibrous layer and a liquid inlet foam layer and the absorbent core includes a transversally central liquid inlet region extending in the longitudinal direction of the absorbent core. Within the liquid inlet region, the liquid inlet foam layer is covered by a plurality of inlet openings and has a transversal width, which is equal to, or up to 9 mm smaller than, the minimum transversal width of the absorbent fibrous layer. The liquid inlet foam layer also has side edge regions arranged in front and rear portions of the absorbent core transversally outside of the liquid inlet region, and within which the liquid inlet foam layer is free from liquid inlet openings.

20 Claims, 3 Drawing Sheets

(51) Int. Cl.
*A61F 13/15* (2006.01)
*A61F 13/513* (2006.01)
*A61F 13/514* (2006.01)
*A61F 13/511* (2006.01)

(52) U.S. Cl.
CPC .............. *A61F 13/51456* (2013.01); *A61F 2013/1591* (2013.01); *A61F 2013/15943* (2013.01); *A61F 2013/15959* (2013.01); *A61F 2013/15967* (2013.01); *A61F 2013/4708* (2013.01); *A61F 2013/5113* (2013.01)

(56) References Cited

U.S. PATENT DOCUMENTS

| | | | |
|---|---|---|---|
| 5,545,155 A * | 8/1996 | Hseih | A61F 13/53747 604/358 |
| 5,817,081 A | 10/1998 | LaVon et al. | |
| 6,413,338 B1 * | 7/2002 | DiPalma | A61F 13/1565 156/253 |
| 2002/0013561 A1 | 1/2002 | Lasko | |
| 2004/0121681 A1 * | 6/2004 | Lindsay | A61F 13/8405 442/121 |
| 2004/0176733 A1 * | 9/2004 | Glaug | A61F 13/534 604/378 |
| 2004/0193129 A1 * | 9/2004 | Guidotti | A61F 13/535 604/378 |
| 2004/0230184 A1 * | 11/2004 | Babusik | A61F 13/53713 604/378 |
| 2005/0096616 A1 | 5/2005 | Arora et al. | |
| 2006/0229579 A1 * | 10/2006 | Wahlstrom | A61F 13/512 604/366 |
| 2008/0140042 A1 * | 6/2008 | Mukai | A61F 13/49001 604/385.23 |
| 2008/0249494 A1 * | 10/2008 | Digiacomantonio | A61F 13/475 604/378 |
| 2011/0004175 A1 | 1/2011 | Veith | |
| 2011/0004176 A1 | 1/2011 | Andersson et al. | |
| 2011/0196330 A1 * | 8/2011 | Hammons | A61F 13/512 604/383 |
| 2013/0289510 A1 * | 10/2013 | Nakajima | A61F 13/49426 604/378 |
| 2014/0295134 A1 | 10/2014 | Wood et al. | |
| 2015/0057632 A1 * | 2/2015 | Luzader | A61F 13/4758 604/385.04 |
| 2015/0133883 A1 | 5/2015 | Cardin et al. | |
| 2015/0133884 A1 * | 5/2015 | Hao | A61F 13/535 604/378 |
| 2015/0148769 A1 * | 5/2015 | Johansson | A61F 13/4751 604/385.23 |
| 2015/0173971 A1 * | 6/2015 | Johansson | A61F 13/4751 604/385.101 |
| 2017/0027778 A1 * | 2/2017 | Stridfeldt | A61F 13/53747 |
| 2018/0161218 A1 * | 6/2018 | Jonegren | A61F 13/476 |
| 2018/0338869 A1 * | 11/2018 | Jonegren | A61F 13/475 |
| 2019/0328588 A1 * | 10/2019 | Saevecke | A61F 13/51104 |

FOREIGN PATENT DOCUMENTS

| | | |
|---|---|---|
| CN | 105828776 A | 8/2016 |
| RU | 2245698 C2 | 2/2005 |
| RU | 2004132048 A | 2/2006 |
| RU | 2296546 C2 | 4/2007 |
| WO | WO-95/10995 A1 | 4/1995 |
| WO | WO-2013/180937 A1 | 12/2013 |
| WO | WO-2015/094068 A1 | 6/2015 |
| WO | WO2015094068 A1 * | 6/2015 |

OTHER PUBLICATIONS

Decision to Grant dated Nov. 27, 2019 issued in Russian patent application No. 2019120845 (10 pages) and its English-language translation thereof (8 pages).

* cited by examiner

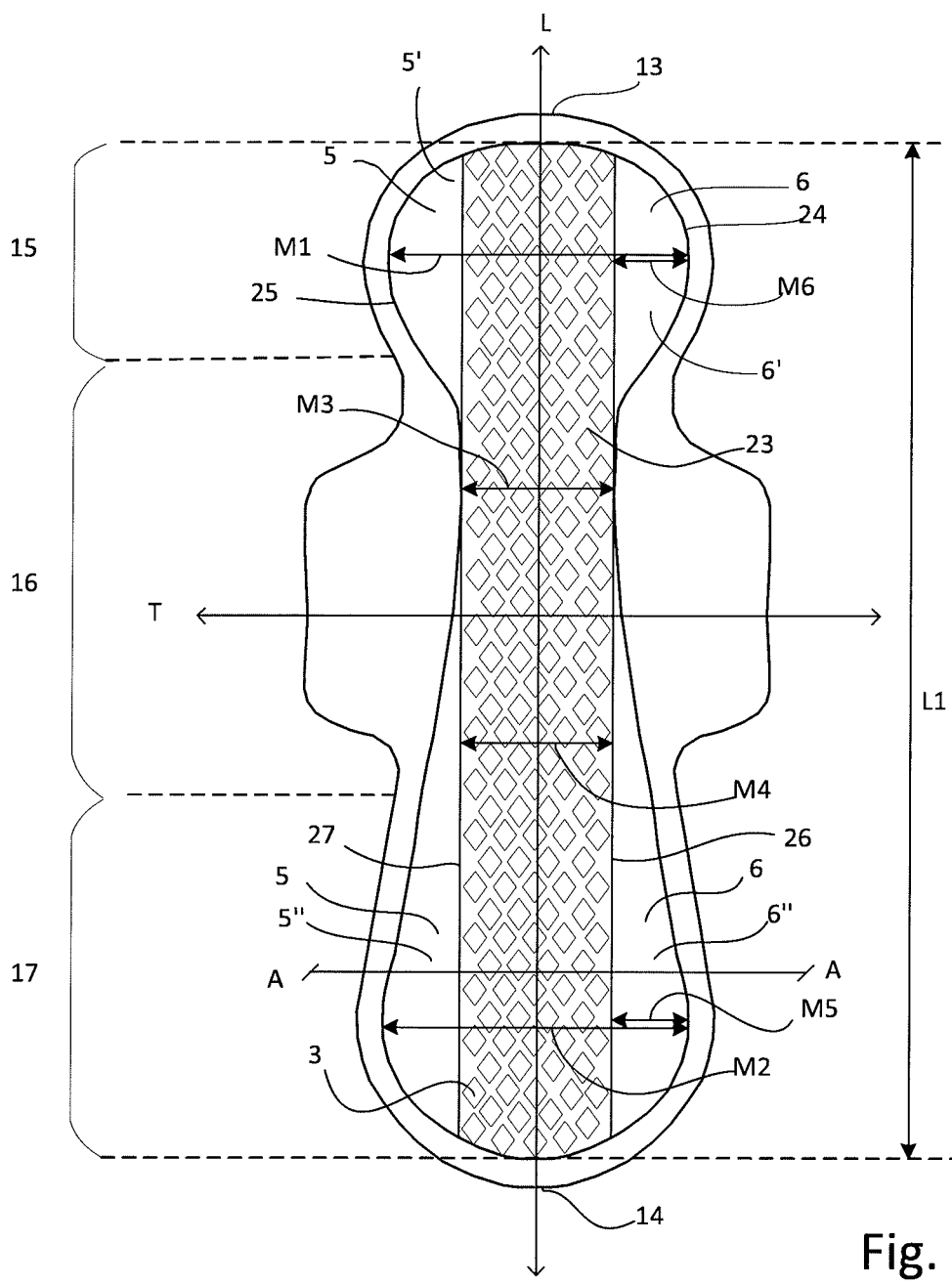
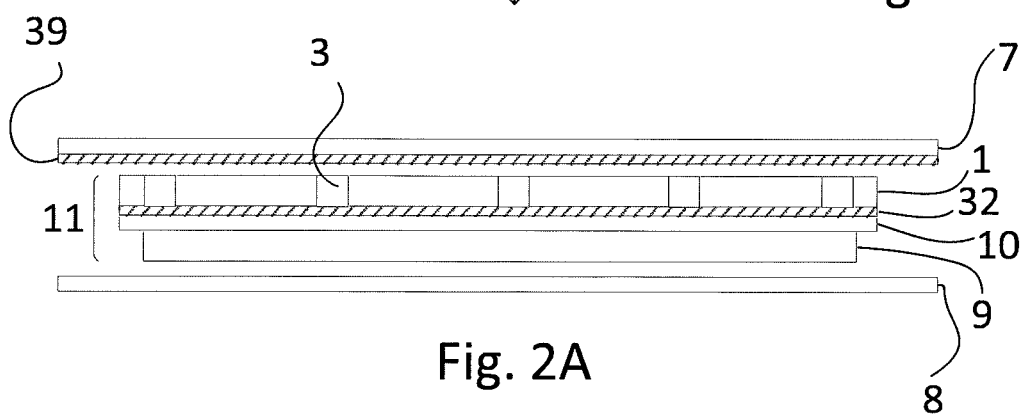
Fig. 1
Fig. 2A

ABSORBENT PRODUCTS COMPRISING FOAM MATERIAL

CROSS-REFERENCE TO RELATED APPLICATION

This application is a § 371 National Stage Application of PCT International Application No. PCT/SE2016/051217 filed on Dec. 5, 2016, which is incorporated herein in its entirety.

TECHNICAL FIELD

The present disclosure relates to an absorbent product, such as a sanitary napkin, including a liquid permeable topsheet, a liquid impermeable backsheet, and an absorbent core enclosed there between, and to a method for manufacturing such absorbent products.

BACKGROUND

For absorbent products such as sanitary napkins there are high requirements that they are discreet, soft and comfortable to wear and at the same time have a reliable security against leakage.

For sanitary napkins intended to absorb menstrual fluid being more viscous than urine, it is often more difficult for the body fluid to reach the absorbent core below the top sheet. Menstrual fluid may easily move around on the user facing side of the top sheet under the influence of gravity, motion and pressure by the user. Migration of menstrual fluid to the edges of the product increases the likelihood of leakage, and further smears the menstrual fluid against the skin of the user making cleanup more difficult. It is desirable that products used for absorbing menstrual fluids are able to give the user a feeling of secureness and a visual impression that the menstrual liquid is absorbed by an absorbent core. Further, it is desired to minimize the cost of manufacturing the absorbent products.

SUMMARY

The present disclosure relates to an absorbent product including a liquid permeable topsheet, a liquid impermeable backsheet, and an absorbent core enclosed between the topsheet and the backsheet. The absorbent core has a length extending in a longitudinal direction of the absorbent product, between a front edge and a rear edge of the absorbent core, and has substantially longitudinally extending side edges. The absorbent core includes a front portion having front maximum transversal width, and a rear portion having a rear maximum transversal width, and has an intermediate minimum transversal width at a point located longitudinally between said front portion and said rear portion. The absorbent core includes an absorbent fibrous layer arranged on the side of the absorbent core, which is closest to the liquid impermeable backsheet, a liquid inlet foam layer arranged on the side of the absorbent core, which is closest to the liquid permeable topsheet. The absorbent core further includes a transversally central liquid inlet region extending in the longitudinal direction of the absorbent core and having substantially longitudinally extending side edges, in which region the liquid inlet foam layer includes a plurality of inlet openings arranged in a pattern, which covers the liquid inlet region. The liquid inlet region has a transversal width, which is equal to, or up to 9 mm smaller than the minimum transversal width of the absorbent fibrous layer.

The above mentioned side edge regions are arranged in said front and rear portions transversally outside of the liquid inlet region, and the liquid inlet foam layer is free from liquid inlet openings in these side edge regions. The transversal width of the liquid inlet region is suitably equal to the minimum transversal width of the absorbent core. The plurality of inlet openings in the liquid inlet foam layer may suitably be formed from a plurality of slits, which have been dilated into openings by transversally extending a web of liquid inlet foam material, from which the liquid inlet foam layer is made, before incorporation into the product. The absorbent core may further include an intermediate portion located between the front and rear portions in the longitudinal direction of the absorbent core, wherein the intermediate minimum transversal width is located within the intermediate portion.

The liquid inlet region may suitably extend longitudinally along 50-100% of the longitudinal length of the absorbent core, or along 80-100%, or along 100% of the absorbent core. Further, the liquid inlet region may have substantially the same width over its entire length. The side edge regions extending between the liquid inlet region and the side edges of the core may have a maximum width of 5.0-50.0 mm, and the side edge regions of the front portion may have a maximum width, which is smaller than a maximum width of the side edge regions of the rear portion.

Further, a carrier layer may advantageously be arranged between the liquid inlet foam layer and the absorbent fibrous layer, which can be made of a nonwoven material or tissue material, or a combination thereof. An adhesive layer can be arranged between the liquid inlet foam layer and the carrier layer, and an additional adhesive layer can be arranged between the liquid inlet foam layer and the topsheet, and the topsheet can then be attached to the carrier layer through the liquid inlet openings.

The distance between adjacent inlet openings may be 1.0 to 5.0 mm, or 1.0 to 9.0 mm, and may have a width in a transversal direction of the absorbent core which is 30-100% of their length in the longitudinal direction of the absorbent core. The plurality of inlet openings may form a combined total open area of 30-80% of the total area of the liquid inlet region.

The present disclosure also relates to a method of manufacturing an absorbent product, including the steps of cutting a plurality of slits in a central region of a continuous web of liquid inlet foam material, said slits extending longitudinally in the machine direction; extending the web of liquid inlet foam material transversally in the cross machine direction, whereby the slits are dilated into openings; applying adhesive to a continuous web of carrier material; combining the continuous web of liquid inlet foam material and the web of carrier material into a combined web; cutting inlet foam layer components from the combined web; providing discrete absorbent components; enclosing the inlet foam layer component and absorbent component between a continuous web of topsheet material and a continuous web of backsheet material; joining at least the topsheet material and the backsheet material along the outer edges of the absorbent product; cutting the combined material into a desired shape, thus obtaining the absorbent product, wherein when extending the web of liquid inlet foam material transversally in the cross machine direction, said web of liquid inlet foam material is extended until the longitudinally central region has a transversal width which is equal to or up to 9 mm smaller than the transversal minimum width of the absorbent core component of the absorbent product, thereby dilating the slits into openings. The web of liquid inlet foam material is suitably transversally extended until the longitudinally central region has a transversal width which is equal to the transversal minimum width of the absorbent core component. Further, the web of liquid inlet foam material is suitably extended to the same degree over its whole longitudinal length. The slits may have a length in the longitudinal direction of 3.0-20.0 mm, or 4.0-16.0 mm, or 5.0-12.0 mm. The method may further include the step of applying adhesive to the surface of the web of topsheet material facing the liquid inlet foam component before enclosing the core components, and pressing the layers together so that the topsheet material layer attaches to the carrier layer through the openings formed in the liquid inlet foam layer.

BRIEF DESCRIPTION OF THE DRAWINGS

FIG. 1 shows a schematic top view of an absorbent product according to the present disclosure.

FIG. 2A shows a schematic cross-sectional view of the product of FIG. 1 across the line A-A in FIG. 1.

DETAILED DESCRIPTION OF PARTICULAR EMBODIMENTS

Figure 2B:
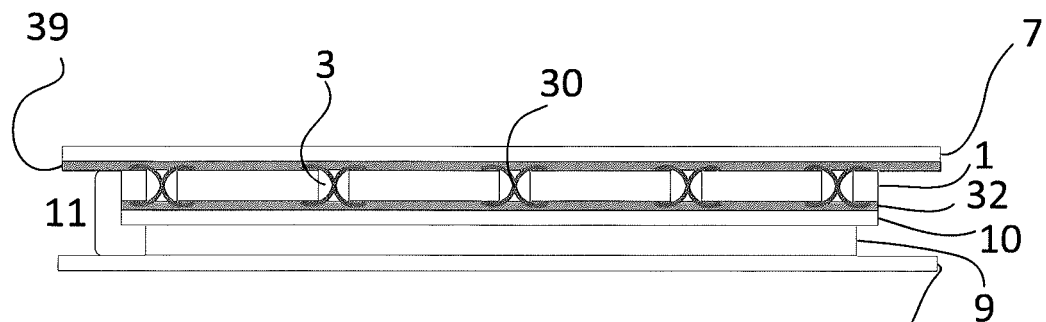
FIG. 2B shows in a schematic cross-sectional view schematically how the topsheet and the carrier layer are attached to each other through the openings in the liquid inlet layer along the line A-A in FIG. 1.

The present disclosure relates to a hygiene absorbent product, such as a sanitary napkin, a panty liner, an incontinence shield, or a diaper. The absorbent product includes an absorbent core disposed between a liquid permeable topsheet and a liquid impermeable backsheet. The absorbent product has a transversal rear end edge intended to be orientated rearwards during use of the absorbent article, and a front end edge intended to be facing forwards towards the abdomen of the wearer. The absorbent core includes an absorbent fibrous layer arranged on the side of the absorbent core, which is closest to the liquid impermeable backsheet, and a liquid inlet foam layer arranged on the side of the absorbent core, which is closest to the liquid permeable topsheet. The absorbent core includes a transversally central liquid inlet region, and front and rear side edge regions are provided transversally outside of the central liquid inlet region in a front and rear portion of the absorbent core, as will be described in more detail below. An absorbent product including a foam material is experienced as soft and is also aesthetically pleasing for many users. The continuous structure of many foam materials gives good pliability and an ability to spring back and to substantially return to its original form after having been exposed to outer loading, which contributes to the wearer comfort.

The absorbent core extends in a longitudinal direction between a front edge and a rear edge, and has substantially longitudinally extending side edges, which are curved so as to give the absorbent core a shape by means of which it includes at least a front portion and a rear portion, and has a has front maximum transversal width within the front portion, and a rear maximum transversal width within the rear portion, and an intermediate minimum transversal width at a point located longitudinally between the front portion and the rear portion, thus giving the absorbent core an hourglass shape. The absorbent core may further include an intermediate portion located between the front and rear portions in the longitudinal direction of the absorbent product, in the crotch part or close to the crotch part, and the intermediate minimum transversal width is then located within the intermediate portion. By providing an intermediate portion having a narrower width than the front and rear portions, the configuration of the absorbent core, and of the absorbent product, can be better adapted to anatomy of the user's body. The crotch part is a portion which is intended to be placed against the crotch of a wearer during use of the product and to constitute the main acquisition area for body fluid that reaches the absorbent product.

The absorbent core includes a transversally central liquid inlet region, which extends in the longitudinal direction of the absorbent core and has substantially longitudinally extending side edges. In the liquid inlet region, the liquid inlet foam layer is provided with a plurality of inlet openings arranged in a pattern, such that the patterns covers the entire area of the liquid inlet region. The central liquid inlet region provided in the liquid inlet foam layer may be located substantially parallel to a longitudinal center line in the longitudinal direction of the absorbent product, and need not follow the outer contour of the absorbent core or the absorbent product. The liquid inlet region may have substantially the same width over its entire length. The liquid inlet foam layer will typically cover the entire absorbent fibrous layer.

The plurality of inlet openings in the liquid inlet foam layer may be formed from a plurality of longitudinally extending slits, which have been dilated into openings by transversally extending a web of liquid inlet foam material from which the liquid inlet foam layer is made, before incorporation into the product, or may be obtained by punching/perforating. Forming the plurality of slits by slitting and extending the inlet foam material has the advantage that no material is cut out from the web, which saves money due to less waste of material, and also improves the handling in the production process by avoiding having a lot of small pieces cut out from the material that may contaminate both the process equipment and the final product.

Due to the lateral extension of the material, the openings formed by slitting and extending the inlet foam material will be widest at their longitudinal center. When the slit is cut as a straight line in the longitudinal direction of the product, the opening will have a diamond shape. The openings can also have other shapes, which can be obtained by cutting slits having a curved shape, e.g. forms as a wave. The longitudinal slit length may be 3.0-20.0 mm, 4.0-15.0 mm or 5.0-12.0 mm. For sanitary napkins intended to absorb menstrual fluid being more viscous than urine, it is often more difficult for the body fluid to reach the absorbent core than for absorbent products intended for urine. Menstrual fluid may easily move around on the user facing side of the top sheet under the influence of gravity, motion and pressure by the user. Migration of menstrual fluid to the edges of the product increases the likelihood of leakage, and further smears the menstrual fluid against the skin of the user making cleanup more difficult. By having a slit length of 5-12 mm, menstrual fluid will reach the absorbent core more easily. The longitudinal length of the dilated openings may differ from the slit length, due to the transversal extension of the foam material, which can decrease the longitudinal length somewhat as the slit are formed into dilated openings.

The inlet openings may have a width in a transversal direction of the absorbent core which is 30-100% of their length in the longitudinal direction of the absorbent core, in order to be large enough to effectively letting through liquid into the absorbent layer.

The openings may have a longer dimension in the longitudinal direction of the absorbent product than in the transversal direction, thus giving the opening a generally oval shape in the longitudinal direction, which gives the user a visual impression of good liquid wicking in the longitudinal direction. The plurality of openings creates a pattern of the openings in the liquid inlet material. The slits may be provided in staggered rows extending in the longitudinal direction, where the slits in each longitudinal row of slits have a longitudinal length A, and are located at a slit distance B between adjacent end points of two sequential slits in the row, and the longitudinal rows are staggered such that adjacent rows are offset by 50% in the longitudinal direction, with a row distance C between two adjacent rows. The distance between adjacent inlet openings in liquid inlet region may be 1.0 to 9.0 mm. A short distance between the openings improves the inlet rate. The liquid inlet foam material may alternatively have other slit patterns, or combinations of different slit pattern. Such slit patterns of the openings may be formed by providing slits with different lengths, or by having slits with different slit distance between the slits. The total open area formed by the slit openings in the horizontal plane of the liquid inlet foam material in the central region may be 30-80% of the total area in the horizontal plane of the liquid inlet foam material in the central region, in order to efficiently let liquid through and at the same time provide sufficient stability.

The transversal width of the liquid inlet region may be equal to the minimum transversal width of the absorbent fibrous layer, or may be up to 9 mm smaller than the minimum transversal width of the absorbent fibrous layer. The liquid inlet region is thus typically not wider than the absorbent core, thus ensuring that any portion of the liquid inlet region is located where a part of the fibrous absorbent layer is present.

A transversal width of the liquid inlet region which is equal to the minimum transversal width of the absorbent core means that the liquid inlet region covers as much of the area as possible in the transversal direction, and in this case no side edges are formed at the location of the minimum transversal width of the absorbent core. This minimizes the amount of inlet foam material needed for manufacture of the absorbent product, since the material from which the liquid inlet foam layer is made is extended until the liquid inlet region has the same width as the absorbent fibrous layer in its narrowest portion.

When the transversal width of the liquid inlet region is up to 9 mm smaller than the minimum transversal width of the absorbent fibrous layer, narrow intermediate side edge regions, in which the liquid inlet foam layer is free from liquid inlet openings, may be formed also in the portion of the absorbent core where it has its minimum transversal width. These intermediate side edge regions may have a width transversally outside the liquid inlet region of up to 4.5 mm (i.e. 0-4.5 mm, where in the case of 0 mm there are no intermediate side edge regions), and can serve to soften the edge of the absorbent core, in in particular in cases where the absorbent fibrous layer is made of a stiff fibrous material, and may also function as liquid edge leakage barriers.

The liquid inlet region may extend longitudinally along 50-100% of the longitudinal length of the absorbent core, in order to allow enough area for effective liquid inlet into the absorbent product. A longitudinal extension of the liquid inlet region of 80-100%, allows effective liquid inlet also when the product is not optimally positioned by the user, and a longitudinal extension of 100% allows for easier manufacture, in addition to the previously mentioned effects, since the liquid inlet region can be provided along an entire longitudinal length of a continuous foam web during manufacture.

Front and rear side edge regions are arranged in the front and rear portions transversally outside of the liquid inlet region, extending between the liquid inlet region and the side edges of the core, and the liquid inlet foam layer is free from liquid inlet openings in these side edge regions. The side edge regions have a smooth surface against the user's skin, due to the absence of openings in the foam.

Due to the hourglass shape, the side edge regions located in the front and rear portions of the absorbent core will be wider than any edge region present at the location of the narrowest width (the minimum transversal width) of the absorbent core. When the width of the central inlet region is substantially equal to the minimum transversal width of the absorbent fibrous layer, and there is thus no side edge region at the narrowest width of the core, the side edge regions of the front and rear portions of the absorbent core will attain the form of cushion like pads, which will contribute to the wearer comfort. Each side edge region of the front and rear portions has a maximum transversal width of 5.0-50.0 mm, or 5.0-20.0 mm.

The side edge regions of the front portion may have a maximum width, which is smaller than a maximum width of the side edge regions of the rear portion, so as to give a more cushioning effect in the rear portion.

The liquid inlet foam material may be hydrophobic or hydrophilic. Hydrophobic foam materials give hydrophobic edge regions, which can function as liquid barriers and will decrease the risk for edge leakage. The plurality of openings present in the central liquid inlet region ensures that the liquid reaches the absorbent layer of the core below the liquid inlet foam layer, even though the foam material is in itself hydrophobic. Also, hydrophobic foam material close to the user's skin may be preferred from a skin care view, since a hydrophobic and dry surface may decrease the risk for bacterial growth and skin irritations.

The foam material may have an open cell structure or a closed cell structure. Foam materials used as liquid inlet layer in absorbent products are often open cell foams, so that liquid can easily enter the foam and consequently also the absorbent core below. However, due to the presence of the plurality of openings in the liquid inlet region, also closed cell foams can be used. In closed cell foams, the liquid will not so easily enter the foam structure itself, and therefore the foam material as such will be kept in a more dry condition, as compared to an open cell foam material, where the pores are connected with each other. The average pore size of the liquid inlet foam material may be greater than the average pore size of the absorbent fibrous layer arranged below the foam, resulting in a pore size gradient and a capillary suction force in the direction from the foam material towards the absorbent fibrous layer below the liquid inlet foam material.

The foam's pliability and flexibility reduces the risk of scrapes. Liquid inlet layers of air laid, cellulose-based layers and liquid inlet layers of non-woven material do not have the same ability to reduce the negative effect of the stiff edges that a stiff cellulose-based absorption layer causes. Flexible foam materials may spring back and return to substantially their original shape after having been exposed to outer loading, and are also pliable. Flexible foam materials also have a padding effect such that the foam material lines the stiff edges and creates a soft distancing element between the user's skin and the stiff edges of the absorbent fibrous layer. The softness and flexibility of a foam material may be of use for example in a premature baby diaper.

Examples of usable foams are polyolefin based foam, polystyrene based foam, PVC foam, polyvinyl alcohol foam, acrylate foam, polyurethane foam, epoxy foam, latex foam, urea-formaldehyde foam, melamine-formaldehyde foam, silicone foam, viscose foam, carboxymethyl cellulose (CMC) foam, starch form, chitosan foam, alginate foam, polyactide foam, polyglycolide foam and polycaprolactone foam.

The liquid inlet foam layer may be held in place by adhesive attachment to any adjacent component, for example the absorbent fibrous layer or the topsheet. The absorbent product may also include a carrier layer arranged between the liquid inlet foam layer and the absorbent fibrous layer.

The liquid inlet foam layer material may be laminated to the carrier layer material in its extended condition so that the foam material is fixed to the carrier material with openings in their extended condition. The absorbent product can include an adhesive layer arranged between the liquid inlet foam layer and the carrier layer, which covers at least an area corresponding to the liquid inlet region, and suitably covers the entire area of the carrier layer, to ensure that the openings within the liquid inlet region are held in a desired position. A suitable construction adhesive is "Adhesive Hotmelt", for example, from Henkel Adhesives, HB Fuller or Bostik. A suitable elastic adhesive is Dispomelt 723U from Henkel Adhesives.

The carrier layer is liquid permeable and can be made of a nonwoven material, such as airlaid or meltblown or spunbond synthetic fibre nonwoven material, or tissue material, e.g. including cellulose fibres, or combinations thereof.

The absorbent product may also include an additional adhesive layer arranged between the liquid inlet foam layer and the topsheet, and wherein the topsheet is attached to the carrier layer through the liquid inlet openings in the liquid inlet region. Thereby, the liquid inlet foam layer will be held from two sides, which allows the open area of the liquid inlet region to be larger, so that the slitted foam material can be extended to a greater degree, which in turn leads to saving foam material.

The liquid inlet foam material and/or the carrier material may be colored. By having different colors in the liquid inlet foam material and the carrier material, the openings in the liquid inlet foam material will be visualized more clearly. Furthermore, if the absorbent core includes an absorbent layer having a shape with a less extension than the foam, a colored layer between the liquid inlet foam layer and the absorbent layer can make the outer contour of the absorbent layer less easy to recognize by the user. A colored carrier layer below the liquid inlet foam layer visualizes the openings more clearly, so that they will be more easily recognized by the user. When a colored carrier layer material is used, it may be desirable to select a topsheet including a see-through material, through which the colored areas or different color is visible. The combined topheet material and foam material may have a maximum opacity, which is sufficiently low for the color difference or colored areas to be visible through both these layers, for example an opacity of 20-70%. A see-through material can be a nonwoven or plastic material, which is sufficiently transparent for the color difference to be visible or at least perceived through the material; or it can be substantially opaque material including apertures through which the color difference is visible, such as an apertured plastic or nonwoven material. The see-through material may also be a textile mesh, having openings between the threads in the material, through which the color difference is visible.

The topsheet layer and the backsheet layer of the absorbent product extend together laterally outside of the absorbent core along the whole circumference thereof. The liquid-permeable top sheet layer is arranged on a body facing surface of the product and is intended to be in contact with the wearer's skin during use. The top sheet layer can be made of any liquid-permeable material known for the purpose, i.e. soft and liquid pervious, such as a layer of nonwoven material or a perforated plastic film, plastic or textile mesh, and fluid permeable foam layers. The top sheet can also be made of a laminate of two or more sheets of the same or different topsheet material, or the top sheet layer can be made of different materials within different parts of the fluid permeable wearer-facing surface. The liquid-impermeable back sheet layer is arranged on a garment facing surface of the product and is intended to be in contact with the garments during use. Backsheet materials that are only fluid repellant may be used in instances where relatively small amounts of body fluids are expected to be taken up. The back sheet layer can be made of a liquid-impermeable plastic film, a nonwoven sheet which has been coated with a liquid barrier material in order to be fluid-impermeable, fluid impermeable foams and fluid impermeable laminates, or any other flexible material sheet which has the ability to withstand liquid penetration. However, it can be advantageous if the liquid-impermeable back sheet layer is breathable, i.e. permits the passage of water vapour through the back sheet. Furthermore, the backsheet may have an outer, garment-facing surface of a textile material such as nonwoven.

The absorbent fibrous layer can be made up of absorbent material, such as cellulose fluff pulp, tissue, etc. and may contain superabsorbents, i.e. polymer materials which are able to absorb body fluid corresponding to many times their own weight and form a hydrogel. The superabsorbents may be mixed with cellulose fluff pulp and/or may be arranged in pockets or layers in the absorbent fibrous layer. The fibres may be pulp fibres and the superabsorbent material may be polyacrylate-based particles.

Moreover, the absorbent core can further include non-absorbent components such as stiffening elements, shaping elements, binders, etc. The absorbent core may for example include absorbent material in the form of an embossed layer including cellulose pulp and superabsorbent particles. The absorbent fibrous layer may suitably have a density of 0.092-0.160 $g/cm^3$ and a basis weight 200-640 $g/m^2$. The absorbent core may further incorporate components for improving the properties of the absorbent core, such as binder fibers, fluid-dispersing materials, wetness indicators etc., as known in the art.

When the above absorbent product is in the form of a sanitary napkin, light incontinence guard or the like, it may further include fastening means for fastening of the absorbent product inside a supporting pant garment, such as a pair of underpants. The fastening means may be in the form of two longitudinally extending bands of pressure sensitive adhesive arranged on the garment-facing surface of the backsheet. The fastening means can be covered by a releasable protective layer, e.g. a siliconized paper, a nonwoven or any other releasable material as is known in the art. Before placing the absorbent product in the supporting pant garment, the protective layer is removed from the fastening means to expose the adhesive and make it available for fastening to the pant garment.

The above absorbent product can be manufactured in various ways. When the central liquid inlet region of the absorbent product is obtained by cutting a pattern of slits and extending the liquid inlet foam material transversely, the inlet foam layer is suitably secured in its extended state, to prevent the dilated openings from returning to a more closed condition. This can be done by means of adhesive attachment, wherein an adhesive is applied to parts of the area of the inlet foam layer itself or to adjacent components. The most effective attachment is obtained when substantially the entire surface are which is in contact with an adjacent component is covered with adhesive, as a fine pattern or as a layer completely covering the surface. If the liquid inlet foam is a perforated non-extended material, the requirements of securing it to adjacent components are lower, but it may still be preferred to secure the foam over its entire surface.

When manufacturing an absorbent product the same materials as described above in relation to the absorbent product can be used.

When the above absorbent product includes a carrier layer, it can be manufactured by means of the following method. The method includes cutting a plurality of slits in a central region of a continuous web of liquid inlet foam material, so that the slits extend longitudinally in the machine direction. The slits can be cut in a pattern, and have lengths and distances in relation to each other as described above in relation to the absorbent product. For example, the slits may have a length in the longitudinal direction of 3.0-20.0 mm, or 4.0-16.0 mm, or 5.0-12.0 mm. After having been slitted, the continuous web of liquid inlet foam material is extended transversally in the cross machine direction, whereby the slits are dilated into openings, having dimensions and patterns as described above in relation to the absorbent product. The extension can be done by grabbing the longitudinal side edges of the material and drawing them transversely away from each other. The web of liquid inlet foam material is extended transversally in the cross machine direction until the longitudinally central region has a transversal width which is equal to or up to 9 mm smaller than the transversal minimum width of the absorbent fibrous core component which is to be included in the absorbent product, thereby dilating the slits into openings. The slitted and extended central region of the continuous web of liquid inlet foam material will form the liquid inlet region in the final absorbent product.

An adhesive is applied to a continuous web of carrier material, and the web of carrier material is combined with the continuous web of liquid inlet foam material into a combined web, which is subsequently cut into inlet foam layer components. The adhesive can be applied to the carrier material by spraying or application by means of slot nozzle equipment. Absorbent fibrous material is provided in the form of discrete absorbent fibrous components, which are combined with the inlet foam layer component and enclosed between a continuous web of topsheet material and a continuous web of backsheet material. At least the topsheet material and the backsheet material are joined along the outer edges of the absorbent product. The resulting combined material is cut into a desired shape, thus obtaining the absorbent product. The absorbent fibrous components can be obtained in any other suitable way, such as by cutting pieces of a desired shape from a continuous web of fibrous absorbent material, or by mat formation.

In order to increase the foam material saving, the web of liquid inlet foam material is transversally extended until the longitudinally central region has a transversal width which is equal to the transversal minimum width of the absorbent core component. The web of liquid inlet foam material may be extended to the same degree over its whole longitudinal length, in order to facilitate the extension step.

The method may also includes applying adhesive to the surface of the web of topsheet material facing the liquid inlet foam component before enclosing the core components, and pressing the layers together so that the topsheet material layer attaches to the carrier layer through the openings formed in the liquid inlet foam layer.

An absorbent product as described above, which does not include a carrier layer, can be manufactured by means of a similar method, with the difference that the liquid inlet foam material web is cut into inlet foam layer components before extending the foam material.

DESCRIPTION OF THE DRAWINGS

FIGS. 1-4 schematically illustrate the above described absorbent product and method by way of example.

FIG. 1 shows top view of an absorbent product in the form of sanitary napkin having a longitudinal direction L and a transversal direction T, and FIG. 2 shows a cross section of the same product. The sanitary napkin of FIG. 1 is depicted with wings, which can as well be omitted. The absorbent product includes a liquid permeable topsheet 7, a liquid impermeable backsheet 8, and an absorbent core 11 enclosed between the topsheet 7 and the backsheet 8. The absorbent core 11 has a length L1 extending in a longitudinal direction of the absorbent product, between a front edge 13 and a rear edge 14 of the absorbent core, and it has substantially longitudinally extending side edges 24, 25. As can be seen in FIGS. 1 and 2, the topsheet 7 and backsheet 8 extend outside of the circumference of the absorbent core 11. The absorbent core 11 includes a front portion 15 having front maximum transversal width M1, and a rear portion 17 having a rear maximum transversal width M2, and the absorbent core 11 further has an intermediate minimum transversal width M3 at a point located longitudinally between said front portion 15 and said rear portion 17. In this embodiment, the absorbent core 11 includes an intermediate portion 16 located between the front portion 15 and the rear portion 17 in the longitudinal direction of the absorbent core 11, and the intermediate minimum transversal width M3 is located within the intermediate portion 16.

As seen best in FIG. 2, the absorbent core 11 includes an absorbent fibrous layer 9 arranged on the side of the absorbent core, which is closest to the liquid impermeable backsheet 8, and a liquid inlet foam layer 1 arranged on the side of the absorbent core, which is closest to the liquid permeable topsheet 7. FIG. 1 shows the absorbent core 11 including a transversally central liquid inlet region 23, which extends in the longitudinal direction of the absorbent core and have substantially longitudinally extending side edges 26, 27, but the distance between these side edges can vary slightly.

The liquid inlet foam layer 1 includes a plurality of inlet openings 3 arranged in a pattern, which covers the liquid inlet region 23. The liquid inlet region 23 has a transversal width M4, which is equal to the minimum transversal width M3 of the absorbent fibrous layer 9, so that side edge regions 5, 6 are arranged in the front and rear portions 15, 17 transversally outside of the liquid inlet region 23. In this example the side edges 16, 27 of the central liquid inlet region 23 are parallel to each other and to the longitudinal axis of the absorbent product, so that the width M4 is the same over its entire length. The side edge regions 5',6' of the front portion 15 have a maximum width M6, and the side edge regions 5",6" of the rear portion 17 have a maximum width M5. In the shown example, the width M6 of the front side edge regions 5',6' is the same as the width M5 of the rear side edge regions 5",6", but the front side edge region width M6 may also be smaller than the rear side edge region width M5.

The absorbent product can include a carrier layer 10 arranged between the liquid inlet foam layer 1 and the absorbent fibrous layer 9, and an adhesive layer 32 arranged between the liquid inlet foam layer 1, and the carrier layer 10. Further, an additional adhesive 39 layer can be arranged between the liquid inlet foam layer 1 and the topsheet 7, and the topsheet 7 can be attached to the carrier layer 10 through the liquid inlet openings 3 by letting the adhesive layers 32, 39 join through the dilated slit openings 3a, which is illustrated in FIG. 2B at the point 30. When the layers of the absorbent product are combined, the carrier layer 10 will adhesively attach to the topsheet layer 7 through the openings 3 in the liquid inlet region 23, by means of the adhesive layers 39, 32.

The liquid inlet foam layer is free from liquid inlet openings in the side edge regions 5, 6. In the shown example, the transversal width M4 of the liquid inlet region 23 is equal to the minimum transversal width M3 of the absorbent core, which means that no side edge regions are present at this location. However, if desired, intermediate side edge regions having a width of up to 4.5 mm may be present transversally outside of the intermediate portion 16.

The plurality of inlet openings 3 provided in the liquid inlet foam layer 1 can be formed from a plurality of slits, which have been dilated into openings by transversally extending a web of liquid inlet foam material, from which the liquid inlet foam layer 1 is made, before incorporation into the product. This is shown in more detail in FIGS. 3A and 3B. In this example, the liquid inlet region 23 extends longitudinally along 100% of the absorbent core 11.

Figure 3A:
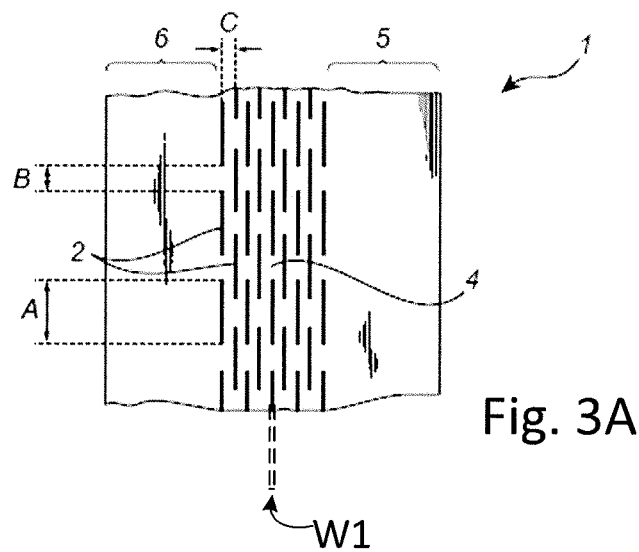
FIG. 3A shows a schematic top view of a liquid inlet foam material before it has been extended.

FIG. 3A shows a top view of a liquid inlet foam material 1 after it has been slitted but before it has been extended, and shows how a pattern of longitudinal slits 2 has been cut. The yet non-extended liquid inlet foam material 1 has in its transversal direction a central region 4 with slits and two side edge regions 5, 6 without slits. The slits 2 in FIG. 3A are straight, but may have any suitable shape such as for example wave-shaped. In the shown example, the slits 2 are provided in a pattern with staggered rows extending in the longitudinal direction of the inlet material 1. The slits 2 are located at a distance B within one longitudinal row, and adjacent rows are arranged at a distance C from each other in the transversal direction. Each slit 2 in the pattern has a slit length A and a width W1.

Figure 3B:
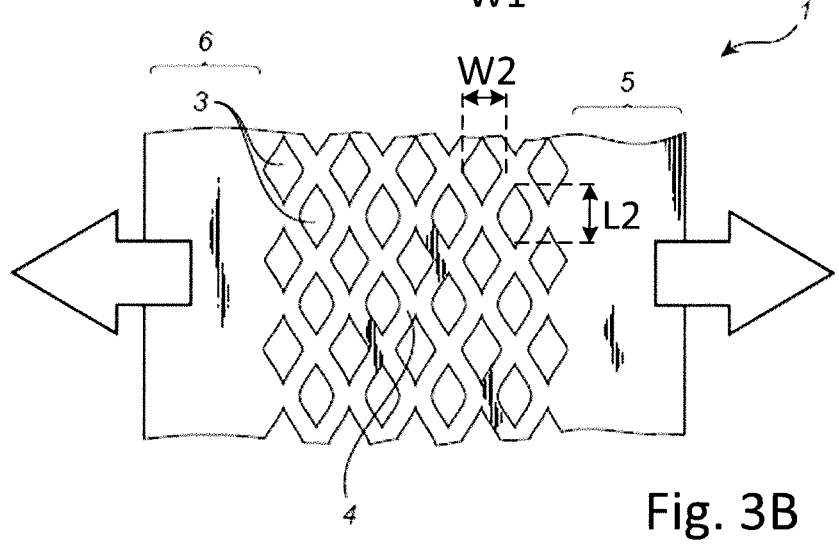
FIG. 3B shows a schematic top view the liquid inlet foam material of FIG. 3A after it has been extended, i.e. after the slits have been dilated to form openings.

FIG. 3B the liquid inlet foam material of FIG. 3A after it has been extended in the direction transversal to the slit 2 direction, i.e. after the slits 2 have been opened to form openings 3. The slits 2 have now been dilated to diamond shaped openings, or diamond pockets, and have a longitudinal length L2 and a transversal width W2. The side edge regions 5, 6 are still free from openings.

Figure 4:
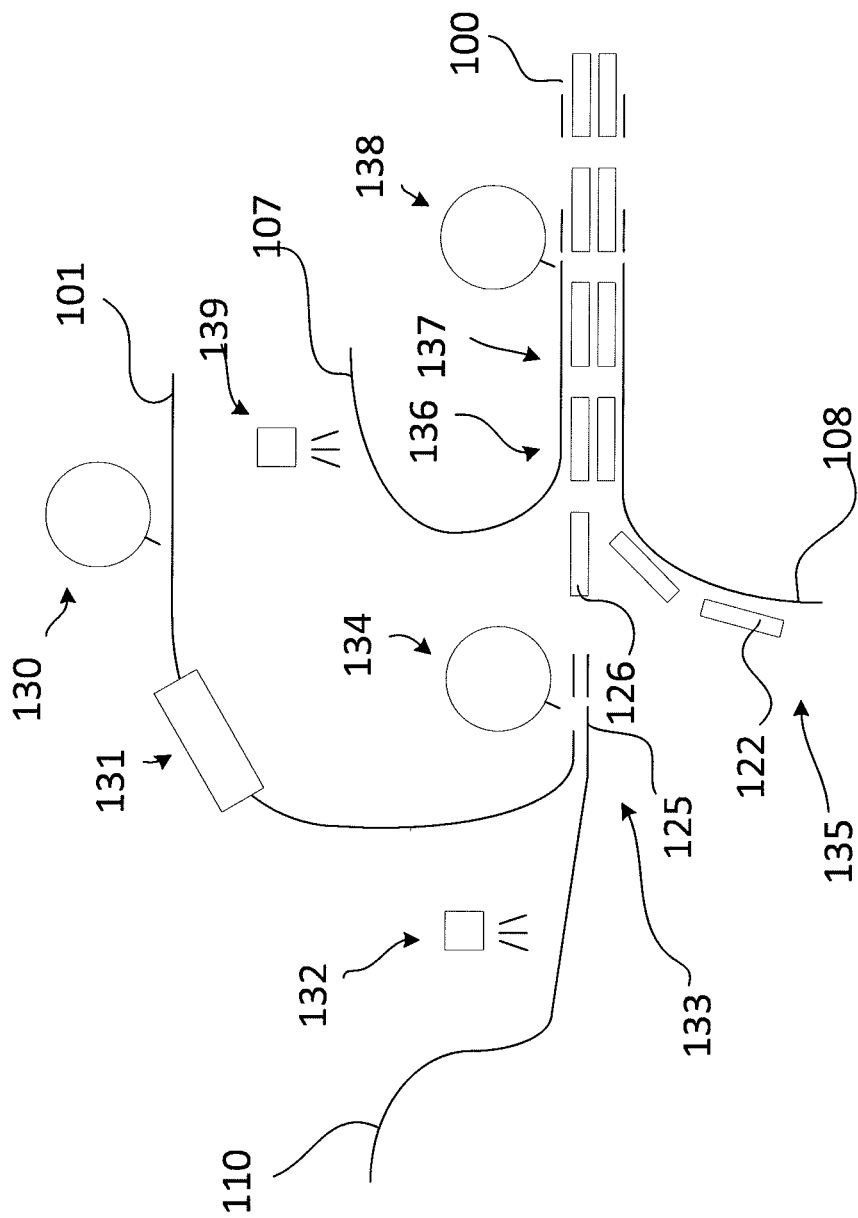
FIG. 4 shows schematically a method of manufacturing an absorbent product comprising an extended liquid inlet foam layer.

FIG. 4 shows schematically a method of manufacturing an absorbent product, comprising
  cutting 130 a plurality of slits 2 in a central region 4 of a continuous web of liquid inlet foam material 101, said slits extending longitudinally in the machine direction;
  extending 131 the web of liquid inlet foam material 101 transversally in the cross machine direction, whereby the slits 2 are dilated into openings 3;
  applying adhesive 132 to a continuous web of carrier material 110;
  combining 133 the continuous web of liquid inlet foam material 101 and the web of carrier material 110 into a combined web 125;
  cutting 134 inlet foam layer components 126 from the combined web 125;
  providing 135 discrete absorbent components 122;
  enclosing 136 the inlet foam layer component 126 and absorbent component 122 between a continuous web of topsheet material 107 and a continuous web of backsheet material 108;
  joining 137 at least the topsheet material 107 and the backsheet material 108 along the outer edges of the absorbent product to form a combined material;
  cutting 138 the combined material into a desired shape, thus obtaining the absorbent product 100, wherein
when extending 131 the web of liquid inlet foam material 101 transversally in the cross machine direction, said web of liquid inlet foam material 101 is extended until the longitudinally central region 4 has a transversal width M4 which is equal to or up to 9 mm smaller than the transversal minimum width M3 of the absorbent core component 122 of the absorbent product 100, thereby dilating the slits 2 into openings 3. The method shown in FIG. 4 also includes applying adhesive 139 to the surface of the web of topsheet material 107 facing the liquid inlet foam component 126 before enclosing the core components 126, 122, and pressing the layers together 135 so that the topsheet material layer 107 attaches to the carrier layer 110 through the openings 3 formed in the liquid inlet foam layer 101.

EXAMPLES

The thickness of a foam layer suitable for the liquid inlet layer is measured with an applied pressure of 0.5 kPa on a non-apertured and non-stretched piece of material. The thickness gauge foot suitably measures 45×45 mm, or in any way it must be smaller than the foam sample. Carefully separate the foam from the article, and measure thickness on a representative area. Lower the foot slowly and gently over the sample, and let it rest for 10 seconds before reading the thickness. In case the foam has an irregular thickness, an average value should be taken from five representative measurement spots.

Density is calculated by weighing the sample (in grams), and then dividing the weight by the sample volume (in $cm^3$). Volume is measured by multiplying the thickness (measured as above) by the sample area. The foam density refers to homogenous foam material, thus excluding any slits or openings.

Opacity is measured according to International Standard ISO 2471:2008(E)—Paper and board—Determination of opacity (paper backing)—Diffuse reflectance method. The method originates from the paper industry, but it is suitable also in this context. Carefully separate the inlet layer from the absorbent product. Measure opacity on an area that is free from slits or apertures. In case the opacity varies over the area of the inlet layer, e.g. due to partial coloration or differences in basis weight, the least opaque area should be considered representative for the inlet layer. The opacity can be defined as:

Opacity (%)=100×(1-intensity of the transmitted light/intensity of emitted light).

Table 1 below shows examples of suitable commercially available foam materials that can be used for the liquid inlet layer of the absorbent core.

TABLE 1

Measurements on foam materials

| | Material designation | Material type | Thickness (mm) | Basis Weight (g/m²) | Density (kg/m³) | Opacity, (%) ISO 2471* |
|---|---|---|---|---|---|---|
| 1 | Recticel Bulfast 35H | Polyurethane foam | 1.96 | 66.9 | 34.1 | 35 |
| 2 | Recticel T23/20 | polyurethane foam | 2.54 | 55.0 | 21.7 | 32 |
| 3 | Recticel T25090 | polyurethane foam | 2.37 | 55.2 | 23.3 | 34 |
| 4 | Recticel T46090 | polyurethane foam | 3.11 | 126.5 | 40.7 | 42 |
| 5 | FXI CAZ080A | polyurethane foam | 1.81 | 57.9 | 32.0 | 53 |

*ISO 2471:2008 (E)-Paper and board-Determination of opacity (paper backing)-Diffuse reflectance method A liquid inlet foam material having low thickness and density is preferred for reasons of comfort and discretion.

The material of sample 5 is a foam having high reflection due to inclusion of white pigment. The foam of sample 4 has relatively high thickness and basis weight, which gives a higher opacity.

The invention claimed is:

1. An absorbent product comprising:
a liquid permeable topsheet,
a liquid impermeable backsheet, and
an absorbent core being comprised of:
    an absorbent fibrous layer arranged on a side of the absorbent core closest to the liquid impermeable backsheet, and
    a liquid inlet foam layer arranged on a side of the absorbent core closest to the liquid permeable topsheet, wherein the absorbent core is enclosed between the topsheet and the backsheet, said absorbent core having a length extending in a longitudinal direction of the absorbent product, between a front edge and a rear edge of the absorbent core, wherein said absorbent fibrous layer includes:
longitudinally extending side edges,
a front portion having a front maximum transversal width,
a rear portion having a rear maximum transversal width,
an intermediate minimum transversal width at a point located longitudinally between said front portion and said rear portion, wherein the intermediate minimum transversal width is smaller than the front maximum transversal width or the rear maximum transversal width,
wherein said liquid inlet foam layer includes:
    a transversally central liquid inlet region extending in the longitudinal direction of the absorbent core and having longitudinally extending side edges, said transversally central liquid inlet region having a transversal width, which is equal to, or up to 9 mm smaller than the minimum transversal width of the absorbent core, and
    side edge regions arranged in said front and rear portions transversally outside of the transversally central liquid inlet region
wherein, within the transversally central liquid inlet, region the liquid inlet foam layer comprises a plurality of liquid inlet openings, but within the side edge regions, the liquid inlet foam layer is free from liquid inlet openings.

2. The absorbent product of claim 1, wherein the transversal width of the transversally central liquid inlet region is equal to the minimum transversal width of the absorbent core.

3. The absorbent product of claim 1, wherein the plurality of liquid inlet openings in the liquid inlet foam layer are formed from a plurality of slits, which have been dilated into openings by transversally stretching a web of liquid inlet foam material, from which the liquid inlet foam layer is made, before incorporation into the absorbent product.

4. The absorbent product of claim 1, wherein the absorbent core further comprises an intermediate portion located between the front portion and the rear portion in the longitudinal direction of the absorbent core, and wherein the intermediate minimum transversal width of the absorbent core is located within the intermediate portion.

5. The absorbent product of claim 1, wherein the transversally central liquid inlet region extends longitudinally along 50-100% of the longitudinal length of the absorbent core.

6. The absorbent product of claim 1, wherein the transversally central liquid inlet region has substantially the same width over its entire length.

7. The absorbent product of claim 1, wherein each of the side edge regions, extending between the transversally central liquid inlet region and the longitudinally extending side edges of the absorbent core, have a maximum width of 5.0-50.0 mm.

8. The absorbent product of claim 7, wherein each of the side edge regions of the front portion has a maximum width, which is smaller than a maximum width of the side edge regions of the rear portion.

9. The absorbent product of claim 1, further comprising a carrier layer arranged between the liquid inlet foam layer and the absorbent fibrous layer.

10. The absorbent product of claim 9, further comprising an adhesive layer arranged between the liquid inlet foam layer and the carrier layer.

11. The absorbent product of claim 10, further comprising an additional adhesive layer arranged between the liquid inlet foam layer and the topsheet, and wherein the topsheet is attached to the carrier layer through the liquid inlet openings.

12. The absorbent product of claim 9, wherein the carrier layer is made of a nonwoven material or tissue material, or a combination thereof.

13. The absorbent product of claim 1, wherein the distance between adjacent liquid inlet openings is 1.0 to 9.0 mm.

14. The absorbent product of claim 1, wherein each of the liquid inlet openings have a width in a transversal direction of the absorbent core which is 30-100% of their length in the longitudinal direction of the absorbent core.

15. The absorbent product of claim 1, wherein the plurality of liquid inlet openings form a combined total open area of 30-80% of the total area of the transversally central liquid inlet region.

16. A method of manufacturing an absorbent product, comprising:
cutting a plurality of slits in a central region of a continuous web of liquid inlet foam material, said slits extending longitudinally in the machine direction;

stretching the web of liquid inlet foam material transversally in the cross machine direction to dilate the slits into openings;
applying adhesive to a continuous web of carrier material;
combining the continuous web of liquid inlet foam material and the web of carrier material into a combined web;
cutting an inlet foam layer component from the combined web;
providing an absorbent component;
enclosing the inlet foam layer component and absorbent component between a continuous web of topsheet material and a continuous web of backsheet material and joining at least the topsheet material and the backsheet material along outer edges of the topsheet material and the backsheet material to form a combined material;
cutting the combined material into a desired shape to obtain the absorbent product,
wherein, when stretching the web of liquid inlet foam material transversally in the cross machine direction, said web of liquid inlet foam material is stretched until the central region has a transversal width which is equal to or up to 9 mm smaller than a transversal minimum width of the absorbent component.

17. The method of claim 16, wherein, when stretching the web of liquid inlet foam material transversally in the cross machine direction, said web of liquid inlet foam material is stretched until the transversal width is equal to the transversal minimum width of the absorbent component.

18. The method of claim 16, wherein, when stretching the web of liquid inlet foam material transversally in the cross machine direction, said web of liquid inlet foam material is stretched to the same degree over its whole longitudinal length.

19. The method of claim 16, wherein the slits have a length in the longitudinal direction of 3.0-20.0 mm.

20. The method of claim 16, further comprising applying adhesive to the surface of the web of topsheet material facing the liquid inlet foam component before enclosing the liquid inlet foam component and the absorbent component within the topsheet material and the backsheet material, and then during the step of joining the top sheet material and the backsheet material to form the combined material, the topsheet material layer is pressed against the liquid inlet foam component such that the topsheet material is attached to the carrier layer through the openings formed in the liquid inlet foam material.

* * * * *